(12) United States Patent
Iida et al.

(10) Patent No.: US 7,348,457 B2
(45) Date of Patent: Mar. 25, 2008

(54) KETOL FATTY ACID DERIVATIVES AND PLANT GROWTH REGULATORS

(75) Inventors: Toshii Iida, Kanagawa (JP); Shoko Yamaguchi, Kanagawa (JP); Mineyuki Yokoyama, Kanagawa (JP); Yoshihiro Yokokawa, Kanagawa (JP); Koji Kobayashi, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 536 days.

(21) Appl. No.: 11/078,335

(22) Filed: Mar. 14, 2005

(65) Prior Publication Data
US 2005/0202974 A1    Sep. 15, 2005

Related U.S. Application Data

(62) Division of application No. 10/239,886, filed as application No. PCT/JP01/02328 on Mar. 23, 2001.

(30) Foreign Application Priority Data
Mar. 26, 2000  (JP) ............................. 2000-128625
Nov. 28, 2000  (JP) ............................. 2000-361216
Mar. 6, 2001   (JP) ............................. 2001-61528

(51) Int. Cl.
*C07C 233/00*  (2006.01)
*C07C 233/45*  (2006.01)

(52) U.S. Cl. ...................... 564/199; 564/123; 564/192; 564/204; 562/400

(58) Field of Classification Search ................ 564/123, 564/192, 199, 204; 562/400
See application file for complete search history.

(56) References Cited
FOREIGN PATENT DOCUMENTS
EP       0 101 588  *  2/1984

* cited by examiner

Primary Examiner—Golam M. M. Shameem
(74) Attorney, Agent, or Firm—Townsend & Banta

(57) ABSTRACT

α-Ketol unsaturated fatty acid derivatives represented by the following formula (1), α-ketol unsaturated fatty acid amide derivatives represented by the following formula (6), and plant growth regulators containing, as the active ingredient, at least one of these derivatives:

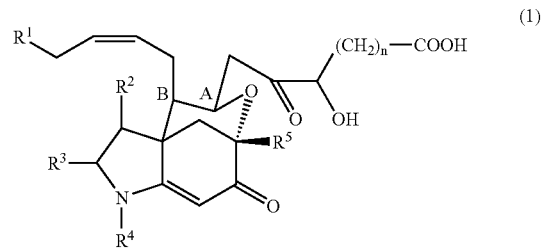

(1)

wherein $R^1$ represents linear $C_{1-5}$ alkyl; R represents hydrogen, etc.; $R^3$ represents hydrogen, etc.; $R^4$ represents hydrogen, etc.; $R^5$ represents hydrogen, etc.; n is an integer from 3 to 15; and the carbon atoms at the A- and B-positions may be in either (R)- or (S)-configuration; and

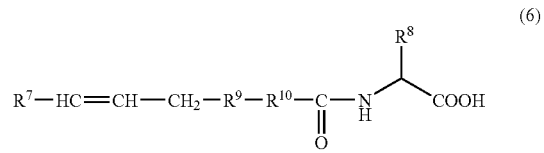

(6)

wherein $R^7$ represents $C_{1-17}$ alkyl, etc; $R^8$ represents hydrogen, etc.; $R^9$ represents α-ketolalkylene; and $R^{10}$ represents specific divalent linear hydrocarbyl.

9 Claims, 7 Drawing Sheets

KETOL FATTY ACID DERIVATIVES AND PLANT GROWTH REGULATORS

CROSS REFERENCE TO A RELATED APPLICATIONS

This is a divisional patent application of co-pending application Ser. No. 10/239,886 filed Dec. 6, 2002, now allowed.

TECHNICAL FIELD

The present invention relates to a specific class of α-ketol fatty acid derivatives and to a process of preparing the derivatives. Moreover, the present invention relates to plant growth regulators making use of the plant growth promoting effect of the derivatives.

BACKGROUND ART

Development of technology to regulate plant growth is a key issue in promoting the supply efficiency of crop plants and horticultural plants.

Among a variety of effects manifested by the regulation of plant growth, promotion of plant growth is a typical effect. Conceivable factors that determine the growth rate of plants include temperature, light, and nutrients. From the past, in order to promote growth of a plant, attempts have been made to select appropriate temperature and light conditions in accordance with the properties of the plant of interest. In addition to such selection of temperature and light conditions, application of a fertilizer is also a well-established technique and has provided a certain effect.

However, effects yielded by application of a fertilizer are limited; i.e., an increased amount of fertilizer does not necessarily attain a growth promotion effect commensurate with such an increase. Contrary to expectations, excessive application of a fertilizer not only hampers the growth of the plant, but possibly raises the risk of pollution of soil.

In particular, in an early stage of plant growth, application of a fertilizer tends to induce nutritional disorder; therefore, application of a fertilizer is typically withheld in this stage.

Therefore, there exists demand for a compound which exhibits plant growth promoting effect and is quite different from conventional fertilizer composed of nitrogen, phosphate, potassium, etc.

There also exists demand for improvement in supply efficiency of crop plants or horticultural plants, through discovery of means for regulating, in accordance with needs, growth of plants, on the basis of various effects, including not only such promotion of plant growth, but also promoted formation of flower buds, retarded aging of plants, prevention of dormancy of plants, and mitigation of plant stresses such as drying and high temperature.

In relation to the above, the present inventors previously found that a certain class of ketol fatty acids exhibits the flower bud formation promoting activity for a broad range of plants (see, for example, Japanese Patent Application Laid-Open (kokai) No. 11-29410). Now, the inventors are in the course of clarifying that such specific ketol fatty acids are intimately involved in various life-related phenomena of plants.

Thus, a primary object of the present invention is to create, as an extension of the mentioned findings regarding the ketol fatty acids, a novel substance which meets the aforementioned subject matter, and to provide a novel plant growth regulator containing the novel substance.

DISCLOSURE OF THE INVENTION

The present inventors have carried out careful studies so as to attain the above object, and quite surprisingly, have found that an α-ketol unsaturated fatty acid derivative, which is formed through bonding of an α-ketol unsaturated fatty acid having a specific structure to norepinephrine (which is one form of catecholamine), and an α-ketol unsaturated fatty acid amide derivative having a specific structure are endowed with excellent plant growth regulating effects, leading to completion of the invention.

Accordingly, in the present application, the inventors provide the following inventions.

A first invention is drawn to an α-ketol unsaturated fatty acid derivative represented by formula (1) (hereinafter the derivative may be referred to as ketol fatty acid derivative I of the invention):

(1)

wherein $R^1$ represents linear $C_{1-5}$ alkyl; $R^2$ represents hydrogen, hydroxyl, methyl, or ethyl; $R^3$ represents hydrogen or carboxyl; $R^4$ represents hydrogen, methyl, ethyl, isopropyl, acetyl, or tert-butyl; $R^5$ represents hydrogen, hydroxyl, methoxy, ethoxy, formyl, or hydroxymethyl; n is an integer from 3 to 15; and the carbon atoms at the A- and B-positions may be in either (R)- or (S)-configuration.

A second invention is drawn to a process of preparing ketol fatty acid derivative I of the invention comprising the steps of mixing an α-ketol unsaturated fatty acid represented by formula (2) (hereinafter the fatty acid may be referred to as α-ketol unsaturated fatty acid (2)) with a catecholamine represented by formula (3) or a derivative thereof (hereinafter may be referred to as catecholamine (3)) and incubating the resultant mixture under neutral to basic conditions, to thereby yield an α-ketol unsaturated fatty acid catecholamine derivative (hereinafter the process may be called the process of the invention):

(2)

wherein $R^1$ and n have the same meanings as defined in relation to formula (1) above, and (3)

wherein $R^2$ to $R^5$ have the same meanings as defined in relation to formula (1) above, and $R^6$ represents hydrogen, linear or branched alkyl, or acyl.

A third invention is drawn to an α-ketol unsaturated fatty acid amide derivative represented by formula (6) (hereinafter the derivative may be referred to as ketol fatty acid derivative II of the invention):

(6)

wherein $R^7$ represents $C_{1-17}$ alkyl or $C_{2-17}$ unsaturated hydrocarbyl having 1 to 5 double bonds (wherein the number of double bonds does not exceed the total number of carbon-carbon bonds); $R^8$ represents hydrogen or a side chain of α-amino acid; $R^9$ represents α-ketolalkylene; and $R^{10}$ represents a divalent linear hydrocarbyl of the following formula:

—$(CH_2)_L$—$(HC=CH)_m$—$(CH_2)_k$— wherein L, m, and k are integers, with m being 0 or 1 and L+k being 1 to 15.

A fourth invention is drawn to a plant growth regulator containing ketol fatty acid derivative I and/or II of the invention as an active component (hereinafter the plant growth regulator may be referred to as the plant growth regulator of the invention or the present plant growth regulator). The present plant growth regulator may assume a variety of forms (such as a flower bud formation promoter, a plant activator, a plant growth promoter, an aging retardant for plants, a flower season extender, a plant dormancy inhibitor, and a plant stress suppressor) on the basis of individual effects of the ketol fatty acid derivative I and/or II of the invention on plants.

As used herein, the expression "plant growth regulation" means regulation, in any form, of life-related activities of a plant, and its concept broadly encompasses not only a variety of plant activating actions, such as plant growth promotion, anti-aging, prolonging of flower season, dormancy inhibition, and imparting of stress resistance to plants, but also promotion of flower bud formation.

Also, the concept of "plant growth promotion" broadly encompasses promoting enlargement of stems and leaves, growth promotion of tubers and root tubers, promotion of fruit bearing, fruit growth promotion, etc.

The present inventors had previously found that the aforementioned α-ketol unsaturated fatty acid (2), alone or in combination with norepinephrine, one form of catecholeamine (3), exhibits flower bud formation promoting activity for a broad range of plants, and had disclosed this in the aforementioned Japanese Patent Application Laid-Open (kokai) No. 11-29410. However, the ketol fatty acid derivatives I and II having a specific chemical structure were found to exhibit excellent plant growth regulatory effect far beyond expectations.

In the present specification, those words which should be expressed in italics (or be underlined) may be expressed in non-italicized letters.

BEST MODES FOR CARRYING OUT THE INVENTION

Modes for carrying out the invention will next be described.

A. Ketol Fatty Acid Derivatives I of the Invention

The ketol fatty acid derivatives I of the invention are α-ketol unsaturated fatty acid derivatives having a structure of formula (1).

As described above, $R^1$ in formula (1) is $C_{1-5}$ linear alkyl, and specific examples thereof include methyl, ethyl, propyl, butyl and pentyl. In the present invention, $R^1$ is preferably methyl.

As described above, $R^2$ is hydrogen, hydroxyl, methyl, or ethyl. In the present invention, $R^2$ is preferably hydroxyl.

As described above, $R^3$ is hydrogen or carboxyl. In the present invention, $R^3$ is preferably hydrogen.

As described above, $R^4$ is hydrogen, methyl, ethyl, isopropyl, acetyl, or tert-butyl. In the present invention, $R^4$ is preferably methyl or hydrogen, with hydrogen being more preferred.

As described above, $R^5$ is hydrogen, hydroxyl, methoxy, ethoxy, formyl, or hydroxymethyl. In the present invention, $R^5$ is preferably hydroxyl or hydrogen, with hydroxyl being more preferred.

As described above, n is an integer from 3 to 15 inclusive. In the present invention, n is preferably an integer from 5 to 9 inclusive, with 7 being more preferred.

As described above, the carbon atoms at the A- and B-positions may be in either (R)- or (S)-configuration. In the present invention, preferably, the carbon atom at the A-position is in (S)-configuration and that at the B-position is in (R)-configuration.

Specific examples of the ketol fatty acid derivative I of the invention include (9R)-11-{(2'S,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9S)-11-{(2'S,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9R)-11-{(2'R,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9R)-11-{(8'S,10'S,11'R)-8'-hydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9R)-11-{(3'S,8'S,10'S,11'R)-3'-carboxy-8'-hydroxy-7'-oxo-11'-[(Z)-2- pentenyl]-9'-oxa-4'-azatricyclo[6.3.1.0$^{1.5}$]dodec-5'-en-10'-yl}-9-hydroxy-10-oxoundecanoic acid, (9R)-11-{(8'S,10'S,11'R)-8'-hydroxy-4'-methyl-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9S)-11-{(3'S,8'S,10'S,11'R)-3'-carboxy-8'-hydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9R)-11-{(3'S,10'S,11'R)-3'-carboxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, (9R)-11-{(2'S,8'S,10'S,11'R)-2',8'-dihydroxy-7'-oxo-11'-[(Z)-2-heptenyl]-9'-oxa-4'-azatricyclo[6.3.1.0$^{1.5}$]dodec-5'-en-10'-yl}-9-hydroxy-10-oxoundecanoic acid, (8R)-10-{(2'S,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-8-hydroxy-9-oxodecanoic acid, (11R)-13-{(2'S,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-11-hydroxy-12-oxotridecanoic acid, (9R)-11-{(2'S,8'S,10'S,11'R)-2',8'-dihydroxy-7'-oxo-11'-[(Z)-2-hexenyl]-9'-oxa-4'-azatricyclo[6.3.1.0$^{1.5}$]dodec-5'-en-10'-yl}-9-hydroxy-10-oxoundecanoic acid, (11R)-13-{(2'S,8'S,10'S,11'R)-2',8'-dihydroxy-7'-oxo-11'-[(Z)-2-hexenyl]-9'-oxa-4'-azatricyclo[6.3.1.0$^{1.5}$]dodec-5'-en-10'-yl}-11-hydroxy-12-oxotridecanoic acid, (9R)-11-{(2'S,8'S,10'R,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid, and (9R)-11-{(2'S,8'S,10'R,11'S)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid.

Of the above-listed compounds, (9R)-11-{(2'S,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid is one of the most preferred species falling in the class of the ketol fatty acid derivatives I of the invention.

The present invention is the first to have identified the ketol fatty acid derivatives I; in the past, the derivatives I had never been identified as either a natural product or a synthesized compound. Also, the derivatives I cannot be produced easily by use of chemical or enzymatic synthesis methods known per se.

The ketol fatty acid derivatives I of the invention exhibit a variety of excellent plant growth regulating activities, and therefore, they can be used as active components of plant growth regulators, which will be described hereinbelow.

A characteristic feature of the ketol fatty acid derivatives I of the invention is that they exhibit much stronger activities than do the aforementioned α-ketol unsaturated fatty acids of formula (2), which would be expected to exhibit similar levels of activities on plants. Specifically, the ketol fatty acid derivatives I of the invention exhibit desired effects when used in an amount about 1/10,000 that of α-ketol unsaturated fatty acids of formula (2).

B. Process of Producing the Ketol Fatty Acid Derivatives I of the Invention

As described above, the process of the invention is drawn to a process of preparing ketol fatty acid derivative I of the invention, and the process comprises the steps of mixing an α-ketol unsaturated fatty acid represented by formula (2) with a catecholamine represented by formula (3) (a typical example of which is norepinephrine) or a derivative thereof and incubating the resultant mixture under neutral to basic conditions, to thereby yield an α-ketol unsaturated fatty acid catecholamine derivative. $R^1$ and n in formula (2) have the same meanings as defined in connection with formula (1). Similarly, $R^2$ to $R^5$ in formula (3) have the same meanings as defined in connection with formula (1). As described above, $R^6$ is hydrogen, linear or branched alkyl, or acyl. In the present invention, $R^6$ is preferably hydrogen, $C_{1-3}$ linear or branched alkyl, or acyl, with hydrogen and methyl being more preferred.

Some α-ketol unsaturated fatty acids (2), at the least, have conventionally been known to be found in animals or plants as intermediates of fatty acid metabolites. Moreover, regarding, for example, 9-hydroxy-10-oxo-12(Z),15(Z)-octadecadienoic acid (hereinafter may be referred to as compound (4)), which is an α-ketol unsaturated fatty acid (2) in which $R^1$ is methyl and n=7, this specific compound has been known as an intermediate of an α-linolenic acid metabolite in wheat (Graveland, Lipids, 8, 606, 1973). Furthermore, the present inventors have found that the aforementioned α-ketol unsaturated fatty acids (2), inclusive of compound (4), alone or in combination with norepinephrine (which is one form of catecholamine), exhibit flower bud formation promoting effect for a broad range of plants (Japanese Patent Application Laid-Open (kokai) No. 11-29410).

Examples of the α-ketol unsaturated fatty acids (2) include 9-hydroxy-10-oxo-12(Z),15(Z)-octadecadienoic acid, 7-hydroxy-8-oxo-10(Z),13(Z)-octadecadienoic acid, 9-hydroxy-10-oxo-12(Z),15(Z)-eicosadienoic acid, 11-hydroxy-12-oxo-14(Z),17(Z)-eicosadienoic acid, and 7-hydroxy-8-oxo-10(Z),13(Z)-nonadecadienoic acid.

Of these α-ketol unsaturated fatty acids (2), those contained in natural products may be obtained by subjecting such natural products to extraction and purification. Alternatively, an α-ketol unsaturated fatty acid (2) of interest may be prepared by adding an enzyme such as lipoxygenase to α-linolenic acid, so as to cause reactions similar to those in the fatty acid metabolism pathway in plants. Further alternatively, an α-ketol unsaturated fatty acid (2) of interest may be prepared through a chemical synthesis method known per se.

A detailed process for the production of α-ketol unsaturated fatty acid (2) is disclosed, for example, in Japanese Patent Application Laid-Open (kokai) No. 11-29410 or by Yokoyama et al. in Plant Cell Physiol., 41, 110-113, 2000.

In the present invention, the catecholamine which is reacted with α-ketol unsaturated fatty acid (2); specifically, the catecholamine of formula (3) or a derivative thereof, is capable of forming an azatricyclo structure represented by formula (1) after having undergone the reaction of the process of the present invention. Specific examples thereof include norepinephrine, epinephrine, dopamine, normetanephrine, 3-O-methyldopamine, and 4-O-methyldopamine.

The mentioned norepinephrine, epinephrine, and other catecholamines (3) may be those commercially available, may be obtained from natural products through extraction and purification, or may be prepared by use of a chemical synthesis method known per se.

In this connection, norepinephrine is well known for its role as a neurotransmitter of the sympathetic nervous system in animals, but in addition to being present in animals, this substance is also known to be present in plants. For example, norepinephrine has been found in a cell suspension of Lemna paucicostata (Takimoto et al., Plant Cell Physiol., 30, 1017-1021, 1991). However, its role has not been completely elucidated.

According to the process of the present invention, a desired derivative of the invention can be obtained by subjecting α-ketol unsaturated fatty acid (2) and catecholamine (3) to incubation under neutral to basic conditions.

As used herein, the expression "neutral to basic conditions" encompasses a broad range of pH values, which would generally occur to those having ordinary skill in the art. Specifically, pH values of not lower than 6.0 or thereabouts are intended, with weakly basic conditions of around pH 8 to 9 being more preferred.

No particular limitation is imposed on the incubation time. Preferably, the incubation time is determined as 1 to 200 hours. Similarly, no particular limitation is imposed on the incubation temperature. Preferably, the incubation temperature is determined as 4 to 40° C.

No particular limitation is imposed on the mixing ratio of α-ketol unsaturated fatty acid (2) and catecholamine (3) which are to be incubated. Preferably, the mixing ratio by weight is 1:10 to 10:1, with 1:1 being most preferred.

Preferably, the reaction medium is water. However, the reaction medium may be a hydrous solvent having a water content of at least 80 mass %. Examples of other solvents which may co-exist in water include methanol, ethanol, and acetone.

Because ketol fatty acid derivative I of the invention exhibits an absorption peak in the vicinity of 300 nm, a UV detector may be employed to detect the derivative I contained in the reaction mixture resulting from an incubation procedure performed in accordance with the process of the invention. After detection, isolation means, such as HPLC, for a certain specified substance may be used, whereby the ketol fatty acid derivative I can be taken up from the reaction mixture through isolation and purification.

Alternatively, isolation and purification of the ketol fatty acid derivative I from the reaction mixture may be performed by use of a method known per se. For example, extraction with a solvent or any of a variety of chromatography techniques may be employed.

C. Ketol Fatty Acid Derivatives II of the Invention

The ketol fatty acid derivatives II of the invention are α-ketol unsaturated fatty acid amide derivatives having a structure of formula (6).

As described above, $R^7$ in formula (6) is $C_{1-17}$ alkyl or $C_{2-17}$ unsaturated hydrocarbyl having 1 to 5 double bonds (wherein the number of double bonds does not exceed the total number of carbon-carbon bonds).

Of the $C_{1-17}$ alkyl groups of $R^7$, examples of linear alkyl groups include methyl, ethyl, propyl, butyl, hexyl, octyl, decyl, dodecyl, tetradecyl, and pentadecyl. Similarly, examples of branched alkyl groups include 2-methyldecyl, 4-ethylhexyl, 10-methyldodecyl, 3,5-diethyldodecyl, 3,6,9-trimethyldecyl, and 2,2-isopropyl-3-methybutyl.

Also, of the $C_{2-17}$ unsaturated hydrocarbyl groups having 1 to 5 double bonds (wherein the number of double bonds does not exceed the total number of carbon-carbon bonds) of $R^7$, examples of linear unsaturated hydrocarbyl groups include 2-hexenyl, 2-pentenyl, 4-octenyl, 2,5-heptadienyl, 3,5-octadienyl, 3,6,11-dodecatrienyl, 1,3,6,8-hexadecatetraenyl, and 3,5,8,10,12-heptadecapentaenyl. Similarly, examples of branched unsaturated hydrocarbyl groups include 3-ethyl-2-octenyl, 4-methyl-3-hexenyl, 7-methy-2,5-decadienyl, 2-ethyl-5,7-dodecadienyl, and 6-(1-propenyl)-8-isopropyl-1,4,9-decatrienyl.

Preferably, $R^7$ in the ketol fatty acid derivative II of the invention is an alkenyl group of the following formula:

$R^{11}$—HC=CH—CH$_2$— wherein $R^{11}$ is $C_{1-7}$ linear alkyl, and preferably ethyl, which has two carbon atoms.

As described above, $R^8$ in formula (6) represents hydrogen or a side chain of α-amino acid. In the case where $R^8$ is a side chain of α-amino acid, no particular limitation is imposed on the species of the amino acid, and examples thereof include glycine, alanine, leucine, isoleucine, tryptophane, tyrosine, glutamine, glutamic acid, asparagine, aspartic acid, lysine, arginine, histidine, cysteine, methionine, serine, phenylalanine, valine, proline, and threonine, regardless of the form L-, D-, or racemic. Of the listed α-amino acids, preferred are L-form neutral amino acids, specifically, L-alanine, L-valine, L-leucine, L-isoleucine, L-phenylalanine, etc., with L-isoleucine being particularly preferred.

As described above, $R^9$ in formula (6) is an α-ketolalkylene group; i.e., a divalent group represented by formula (7) or (8) shown below, with the case of formula (7) being preferred, wherein the carbon atom on the amide bonding side of $R^9$ is bonded to a hydroxyl group.

(7)

(8)

As described above, $R^{10}$ in formula (6) is a divalent linear hydrocarbyl group of the following formula:

—(CH$_2$)$_L$—(HC=CH)$_m$—(CH$_2$)$_k$— wherein L, m, and k are integers, with m being 0 or 1 and L+k being 1 to 15 inclusive. Preferably, m is 0 and L+k is 3 to 10 inclusive, and more preferably, m is 0 and L+k is 7.

Preferably, double bonds contained in the ketol fatty acid derivative II of the invention are of the cis-form. Specifically, the following double bonds:

the double bond appearing in $R^7$ of $R^{11}$—HC=CH—CH$_2$—, the double bond appearing in $R^{10}$ when m=1, and the double bond appearing in the moiety $R^7$—HC=CH—CH$_2$— of the ketol fatty acid derivative II of the invention, are preferably of the cis-form.

A ketol fatty acid derivative II of the invention contain a plurality of asymmetric carbon atoms, and any of the stereoisomers attributed to those asymmetric carbon atoms falls within the definition of the ketol fatty acid derivative II of the invention. Thus, the ketol fatty acid derivatives II of the invention may be optical isomers derived from optical resolution or may be mixtures of such isomers.

Specific examples of the ketol fatty acid derivative II of the invention include N-[9-hydroxy-10-oxo-12(Z),15(Z)-octadecadienoyl]-L-isoleucine, N-[9-hydroxy-10-oxo-12(Z),15(Z)-octadecadienoyl]-L-serine, N-[9-hydroxy-10-oxo-12(Z),15(Z)-octadecadienoyl]-L-asparagine, N-[9-hydroxy-10-oxo-12(Z),15(Z)-octadecadienoyl]-L-leucine, N-[9-hydroxy-10-oxo-12(Z),15(Z)-octadecadienoyl]-L-histidine, N-[9-hydroxy-10-oxo-12(Z),15(Z)-octadecadienoyl]-glycine, N-[9-hydroxy-10-oxo-12(Z),15(Z)-octadecadienoyl]-D-isoleucine, N-[9-hydroxy-10-oxo-12(Z)-octadecaenoyl]-L-isoleucine, N-[13-hydroxy-12-oxo-9(Z),15(Z)-octadecadienoyl]-L-valine, N-[13-hydroxy-12-oxo-9

(Z),15(Z)-octadecadienoyl]-D-alanine, N-[9-hydroxy-10-oxo-12(Z),15(Z)-eicosadienoyl]-L-isoleucine, N-[9-hydroxy-10-oxo-12(Z),15-hexadecadienoyl]-L-isoleucine, N-[9-hydroxy-10-oxo-6(Z),12(Z)-octadecadienoyl]-L-leucine, N-[9-hydroxy-10-oxo-12(E),15(E)-octadecadienoyl]-L-isoleucine, N-[9-hydroxy-10-oxo-12(E),15(E)-octadecadienoyl]-D-leucine, N-[9-hydroxy-10-oxo-6(Z),12(Z),15(Z)-octadecatrienoyl]-L-isoleucine, N-[9-hydroxy-17-methyl-10-oxo-12(Z),15(Z)-octadecadienoyl]-L-isoleucine, N-[9-hydroxy-17-methyl-10-oxo-12(Z),15(Z)-octadecadienoyl]-D-aspartic acid, and N-[15,17-dimethyl-9-hydroxy-10-oxo-12(Z)-octadecaenoyl]-L-isoleucine.

Of these listed ketol fatty acid derivatives II of the invention, N-[9-hydroxy-10-oxo-12(Z),15(Z)-octadecadienoyl]-L-isoleucine is one of best preferred, because it satisfies all the above-mentioned preferred conditions.

The ketol fatty acid derivatives II of the invention are endowed with a variety of excellent plant growth regulating effects, and therefore, can be used as an active ingredient of plant growth regulators, which are employed for activating plants, as described hereinbelow.

A characteristic feature of the ketol fatty acid derivatives II of the invention is that they exhibit much stronger activities than do α-ketol unsaturated fatty acids disclosed in Japanese Patent Application Laid-Open (kokai) No. 11-29410, which are represented by formula (6) whose amino acid moiety (—NH—CHR$^8$—COOH) is replaced by a hydroxyl group (—OH). In other words, the ketol fatty acid derivatives II of the invention exhibit much stronger activities than do α-ketol unsaturated fatty acids (2), which would be expected to exhibit similar levels of activities on plants.

It should be noted that the ketol fatty acid derivatives II of the invention had never been identified as either a natural product or a synthesized compound.

The ketol fatty acid derivatives II of the invention can be produced by a process which accords with the specific chemical structure of the derivatives of interest. For example, the ketol fatty acid derivatives II can be produced by causing the 1-position carboxyl of α-ketol unsaturated fatty acid (2) to be bonded to the amino group of α-amino acid.

Some α-ketol unsaturated fatty acids (2), at the least, which may serve as starting substances in the production of the ketol fatty acid derivatives II of the invention, have conventionally been known to be found in animals or plants as intermediates of fatty acid metabolites. Moreover, the present inventors has already found that the above-mentioned α-ketol unsaturated fatty acids (2), such as 9-hydroxy-10-oxo-12(Z),15(Z)-octadecadienoic acid, exhibit flowe bud formation promoting effect (Japanese Patent Application Laid-Open (kokai) No. 11-29410).

Examples of the α-ketol unsaturated fatty acids (2) include 9-hydroxy-10-oxo-12(Z),15(Z)-octadecadienoic acid, 7-hydroxy-8-oxo-10(Z),13(Z)-octadecadienoic acid, 9-hydroxy-10-oxo-12(Z),15(Z)-eicosadienoic acid, 11-hydroxy-12-oxo-14(Z),17(Z)-eicosadienoic acid, and 7-hydroxy-8-oxo-10(Z),13(Z)-nonadecadienoic acid.

Of these α-ketol unsaturated fatty acids (2), those contained in natural products may be obtained by subjecting such natural products to extraction and purification. Alternatively, an α-ketol unsaturated fatty acid (2) of interest may be prepared by adding an enzyme such as lipoxygenase to α-linolenic acid, so as to cause reactions similar to those in the fatty acid metabolism pathway in plants. Further alternatively, an α-ketol unsaturated fatty acid (2) of interest may be prepared through a chemical synthesis method known per se.

A detailed process for the production of α-ketol unsaturated fatty acid (2) is disclosed, for example, in Japanese Patent Application Laid-Open (kokai) No. 11-29410 or by Yokoyama et al. in Plant Cell Physiol., 41, 110-113, 2000.

Bonding between the 1-position carboxyl of α-ketol unsaturated fatty acid (2) and the amino group of α-amino acid may be achieved through a technique known per se. For example, as is described in literature such as "Lectures on Experimental Chemistry 22, Organic Synthesis IV. Acids, Amino Acids, and Peptides" pp. 259-271 (edited by the Chemical Society of Japan, published by Maruzen Co., Ltd., 1992) and "Fundamentals and Experiments of Peptide Syntheses" authored by IZUMIYA, Nobuo, et al., pp. 89-125 (Maruzen Co., Ltd., 1985), there may be employed the condensation method, the active esterification method, the azide method, or the mixed acid anhydride method.

When the condensation method is employed, example condensing agents which may be used include dicyclohexylcarbodiimide (DCC), diisopropylcarbodiimide (DIPC), 1-ethyl-3-(3-dimethylaminopropyl)carbodiimide (WSC) or a hydrochloric salt thereof, benzotriazol-1-yl-tris(dimethylamino)phosphonium hexafluorophosphate (BOP), and diphenylphosphorylazide (DPPA). If necessary, 1-hydroxybenzotriazole (HOBt), N-hydroxysuccinimide (HONSu), 3-hydroxy-4-oxo-3,4-dihydro-1,2,3-benzotriazine (HOOBt), or the like compound may be employed as an additive.

For example, a target ketol fatty acid derivative II may be obtained through the following process. Firstly, α-ketol unsaturated fatty acid (2) and α-amino acid are dissolved in a solvent such as DMF. The resultant solution is allowed to react in the presence of a condensing agent or a combination of a condensing agent and an additive. Subsequently, the reaction mixture is subjected to further treatments such as concentration and purification.

When the active esterification method is employed, there may be used p-nitrophenol, N-hydroxysuccinimide, pentafluorophenol, etc. Briefly, a p-nitrophenyl ester (ONp), an N-hydroxysuccinimide ester (ONSu), a pentafluorophenyl ester (OPfp), or a similar ester of α-ketol unsaturated fatty acid is formed, and the ester is subjected to a condensation reaction with an amino acid of interest, whereby a target ketol fatty acid derivative II is obtained.

When the azide method is performed, hydrazine, anhydrous hydrazine, or a similar substance may be employed. Through the process, a hydrizide of α-ketol unsaturated fatty acid is obtained. Subsequently, by use of, for example, butyl nitrite or tert-butyl nitrite, an azide is obtained, which is subjected to a condensation reaction with an amino acid of interest, whereby a target ketol fatty acid derivative II is obtained.

When the mixed acid anhydride method is performed, isobutyloxycarbonyl chloride, diethylacetyl chloride, trimethylacetyl chloride, or a similar substance may be employed. Through the process, an anhydride of α-ketol unsaturated fatty acid is formed, which is subsequently subjected to a condensation reaction with an amino acid of interest, whereby a target ketol fatty acid derivative II is obtained.

When any of the above reactions for preparing the ketol fatty acid derivative II of the invention is performed, according to needs, a protective group may be introduced and ultimately removed.

Thus, the ketol fatty acid derivatives II of the invention having a variety of excellent plant growth regulating effects can be prepared.

D. The Plant Growth Regulator of the Invention

When applied to a plant, the plant growth regulator of the invention can regulate the growth of the plant.

By the expression "plant growth regulation" or "regulation of plant growth," the following effects, among other effects, are contemplated.

(a) Flower Bud Formation Promoting Effect

Administration of the plant growth regulator of the invention to a plant in need thereof promotes formation of flower buds of the plant. That is, by the application of the plant growth regulator of the invention, formation of flower buds—which precede flowering of the plant—can be induced.

In this sense, the present invention provides an agent exerting a more specified effect of "promotion of flower bud formation of a plant" (flower bud formation promoter).

When the plant growth regulator of the invention is applied to a plant in expectations of promoting flower bud formation, no particular limitation is imposed on the timing of administration, so long as the administration is performed before the formation of flower buds. Preferably, the regulator is administered to a plant while the plant undergoes other treatment suitable for the plant. For example, in the case of a short-day plant such as morning glory (*Pharbitis nil*), preferably, administration of the plant growth regulator of the invention is performed in combination with a predetermined dark period treatment.

(b) Plant Activating Effect

Through administration of the plant growth regulator of the invention to a plant, the life-related activities of the plant can be activated.

Specifically, examples of such plant activators include plant growth promoters, anti-aging agents, dormancy preventive agents, and anti-stress agents.

(b)-1: Plant Growth Promoting Effect

When the plant growth regulator of the invention is used as a plant activator, it accelerates the growth rate of the plant to thereby improve harvest efficiency, etc.; i.e., the plant growth regulator of the invention may be used as a plant growth promoter. (As described hereinabove, attainable effects in this case include enlargement in stems and leaves, growth promotion of tubers and root tubers, promotion of fruit bearing, and fruit growth promotion). In this sense, the present invention provides an agent exerting a more specified effect of "promotion of plant growth" (plant growth promoter).

When the plant growth regulator of the invention is applied to a plant for the purpose of activating the plant, a notable effect occurs; growth of a plant can be accelerated in an early stage after germination, which previously had been difficult to attain by use of a fertilizer.

Therefore, when the plant growth regulator of the invention is used as a plant growth promoter, it is recommended that the regulator be administered at the time of seeding or during an early stage of growth of a plant after germination.

That is, simple administration, by spraying or any other means, of the plant growth regulator of the invention during an early stage of growth of a plant after germination persistently promotes the growth of the plant. Also, even when the plant growth regulator of the invention is used excessively, plant growth disorder is observed only in rare cases, as contrasted with case of excessive application of fertilizers, and therefore, the plant growth regulator can be used without paying strict attention to the amount applied.

In the fields of horticulture or agriculture, instead of seeds, whose handling is troublesome after delivery thereof, distribution in the form of seedlings is now becoming mainstream. In particular, most amateur flower gardeners purchase seedlings rather than seeds from ornamental flower businesses. Thus, if the plant growth regulator is used before trading or distribution of the seedlings, well-grown seedlings can be put on the market.

The above-described properties of the plant growth regulator of the invention are advantageously used for attaining increased yields of leafy vegetables, such as spinach, lettuce, and cabbage.

(b)-2: Anti-Aging Effect

The plant growth regulator of the invention may be used as a plant activator, which is an agent capable of activating a plant by retarding aging. Specifically, the regulator of the invention can prolong the flowering period, whereby people can enjoy flowers for a longer period, or whereby the pollination period can be extended. The present invention also provides "flowering period extenders" on the basis of such an individual effect; i.e., an effect of extending the flowering period. In addition, administration of the plant growth regulator of the invention can increase the number of flowers per plant.

When the plant growth regulator of the invention is employed as a plant activator in expectation of prolonging the flowering period, the regulator can be administered to a plant at any time, including the flowering period of the plant. Specifically, administration may be performed while seeds are soaked in water or after germination.

As is sometimes experienced with the case of annual plants, when a plant becomes very weak and withers, administration of the plant growth regulator of the invention to such a plant can delay withering (or aging) of the plant.

Thus, the plant growth regulator of the invention exerts the specific effects of "flowering period prolonging effect" and "life-extending effect" on plants; in other words, a "plant aging retarding effect" on plants, to thereby activate the plants.

Thus, the present invention also provides an agent exerting a specific "plant aging retarding effect" among other plant activating effects (plant aging retardant).

(b)-3: Dormancy Inhibiting Effect

Through administration of the plant growth regulator of the invention to a plant, the plant can be prevented from falling into a dormant state, whereby the plant can be activated. Specifically, when the plant growth regulator of the invention is used as a plant activator, the "dormancy period," during which growth of a plant is stopped for a certain period because of deterioration of the growth environment, can be shortened or terminated.

In this sense, the present invention also provides an agent exerting a specific "plant dormancy inhibiting effect" (plant dormancy inhibitor).

When the plant growth regulator of the invention is used as a plant activator in expectation of inhibiting dormancy of a plant, administration thereof is preferably performed in an early stage after germination of the plant, to thereby successfully prevent the plant from falling dormant. In this connection, when the plant growth regulator is administered to a plant which has already fallen into dormancy, the plant can be revived.

(b)-4: Anti-Stress Effect

Administration of the plant growth regulator of the invention to a plant can impart stress resistance to the plant, thereby activating the plant. Plants are under a variety of stresses, including dryness, high temperature, low temperature, osmotic pressure, and so on. Thus, by use of the plant growth regulator of the invention, stresses imposed on plants by climate changes or by germination-inducing treatment—which may lower the harvest yield of cultivated plants—can be mitigated, whereby the plants can be activated.

In this sense, the present invention also provides an agent that exerts a specific "stress mitigating effect" on plants (plant stress suppressor).

When the plant growth regulator of the invention is used as a plant activator in expectation of suppressing plant stress, administration thereof is preferably performed when germination of plant seeds is induced, or after germination, to thereby successfully impart to the plant resistance against stresses.

No particular limitation is imposed on the upper limit of the administration amount of the active agent of the plant growth regulator of the invention, ketol fatty acid derivative I or II. That is, even when the ketol fatty acid derivative I or II, as contained in the plant growth regulator of the invention, is administered to a plant in large amounts, negative effects on the plant, such as growth disturbance, are rarely observed. Thus, as compared with the case of conventional plant hormonal agents, which produce considerable negative effects if administered in excessive amounts, and thus require careful control of the amount to be administered, the plant growth regulator of the invention is understood to be a remarkably excellent agent.

The lower limit of the administration amount of the ketol fatty acid derivative I or II may differ depending on the identity or size of individual plants. As a general tip, the lower limit for ketol fatty acid derivative I would be 0.1 nM, and that for ketol fatty acid derivative II would be 0.01 µM, for a single plant per administration.

The amount of ketol fatty acid derivative I or II to be incorporated into the plant growth regulator of the invention can be determined in accordance with the manner of use, the identity of the plant to which the regulator is applied, the specific product form of the regulator, and other factors. The ketol fatty acid derivative I or II per se may be used as the plant growth regulator of the invention. In consideration of the typical dose of the ketol fatty acid derivative I or II, when ketol fatty acid derivative I is incorporated into the regulator, the amount of the derivative I is preferably about 0.1 ppb to about 1 ppm, more preferably about 1 ppb to about 100 ppb, on the basis of the entirety of the regulator. When ketol fatty acid derivative II is incorporated into the regulator, the amount of the derivative II is preferably about 10 ppb to about 100 ppm, more preferably about 100 ppb to about 10 ppm, on the basis of the entirety of the regulator.

Examples of the product form of the plant growth regulator of the invention include solutions, solid agents, powders, and emulsions. In accordance with the product form, the plant growth regulator of the invention may appropriately contain known pharmaceutically acceptable carrier components and auxiliary agents for drug production, so long as they do not impede the intended effect of the present invention; i.e., plant growth promoting effect. When the plant growth regulator of the invention assumes the form of powders or solid agents, for example, the following carrier components may be incorporated: inorganic substances such as talc, clay, vermiculite, diatomaceous earth, kaolin, calcium carbonate, calcium hydroxide, terra alba, and silica gel; and solid carriers such as flour and starch. When the plant growth regulator of the invention assumes the form of solutions, for example, the following carrier components may be incorporated: liquid carriers including water; aromatic hydrocarbons such as xylene; alcohols such as ethanol and ethylene glycols; ketones such as acetone; ethers such as dioxane and tetrahydrofuran; dimethylformamide; dimethyl sulfoxide; and acetonitrile. Examples of the auxiliary agents for drug production which may be incorporated include anionic surfactants such as alkyl sulfates, alkyl sulfonates, alkyl aryl sulfonates, dialkyl sulfosuccinates; cationic surfactants such as salts of higher aliphatic amines; nonionic surfactants such as polyoxyethylene glycol alkyl ethers, polyoxyethylene glycol acyl esters, polyoxyethylene polyalcohol acyl esters, and cellulose derivatives; thickeners such as gelatin, casein, gum arabi; extenders; and binders.

If desired, the plant growth regulator of the invention may further contain typical plant growth controlling agents, benzoic acid, nicotinic acid, nicotinamide, and pipecolic acid, so long as they do not impede the intended effects of the present invention.

The plant growth regulator of the invention may be applied to various plants in a manner in accordance with the product form of the regulator. For example, the plant growth regulator of the invention may be sprayed, dropped, or applied, in the form of solution or emulsion, to the point of growth of a plant, to a portion of the plant, such as stem or leaf, or to the entirety of the plant; or may be absorbed, in the form of solid agent or powder, in the root of the plant via earth. Alternatively, when the plant growth regulator of the invention is used for promoting growth of a water plant such as duckweed, the regulator may be absorbed in the root of the water plant, or the regulator in the form of solid agent may be gradually dissolve in the water.

The frequency of application of the plant growth regulator of the invention to a plant varies with the type of the plant or the purpose of application. Basically, desired effects can be obtained through merely a single application. When the regulator is applied several times, application is preferably performed at an interval of one week or more.

No particular limitation is imposed on the type of plants to which the plant growth regulator of the invention can be applied, and the regulator is effective for angiosperms (dicotyledons and monocotyledons), fungi, lichens, bryophytes, ferns, and gymnosperms.

Examples of dicotylendos of angiosperms include Convolvulaceae such as *Convolvulus* (*C. nil* L.; *Pharbitis nil*), *Calystegia* (*C. japonica, C. hederacea*, and *C. soldanella*), *Ipomoea* (*I. pes-caprae*, and *I. batatas*), and *Cuscuta* (*C. japonica*, and *C. australis*), Caryophyllaceae such as *Dianthus, Stellaria, Minuartia, Cerastium, Sagina, Arenaria, Moehringia, Pseudostellaria, Honkenya, Spergula, Spergularia, Silene, Lychnis, Melandryum*, and *Cucubalus*, and furthermore, Casuarinaceae, Saururaceae, Piperaceae, Chloranthaceae, Salicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Aristolochiaceae, Mitrastemonaceae, Balanophoraceae, Polygonaceae, Chenopodiaceae, Amaranthaceae, Nyctaginaceae, Theligonaceae, Phytolaccaceae, Aizoaceae, Portulacaceae, Magnoliaceae, Trochodendraceae, Cercidiphyllaceae, Nymphaeaceae, Ceratophyllaceae, Ranunculaceae, Lardizabalaceae, Berberidaceae, Menispermaceae, Calycanthaceae, Lauraceae, Papaveraceae, Capparaceae, Brassicaceae (*Crusiferae*), Droseraceae, Nepenthaceae, Crassulaceae, Saxifragaceae, Pittosporaceae, Hamamelidaceae, Platanaceae, Rosaceae, Fabaceae (*Leguminosae*), Oxalidaceae, Geraniaceae, Linaceae, Zygophyllaceae, Rutaceae, Simaroubaceae, Meliaceae, Polygolaceae, Euphorbiaceae, Callitrichaceae, Empetraceae, Coriariaceae, Anacardiaceae, Aquifoliaceae, Celastraceae, Staphyleaceae, Icacinaceae, Aceraceae, Hippocastanaceae, Sapindaceae, Sabiaceae, Balsaminaceae, Rhamnaceae, Vitaceae, Elaeocarpaceae, Tiliaceae, Malvales, Sterculiaceae, Actinidiaceae, Theaceae, Clusiaceae (*Guttiferae*), Elatinaceae, Tamaricaceae, Violaceae, Flacourtiaceae, Stachyuraceae, Possifloraceae, Begoniaceae, Cactaceae, Thymelaeaceae, Elaeagnaceae, Lythraceae, Punicaceae, Rhizophoraceae, Alangiaceae, Melastomataceae, Trapaceae, Onagraceae, Haloragaceae, Hippuridaceae, Araliaceae, Apiaceae (*Umbelliferae*), Cornaceae, Diapensiaceae, Clethraceae, Pyrolaceae, Ericaceae, Myrsinaceae, Primulaceae, Plumbaginaceae, Ebenaceae, Symplocaceae, Styracaceae, Oleaceae, Buddlejaceae, Gentianaceae, Apocynaceae, Asclepiadaceae, Polemoniaceae, Boraginaceae, Verbenaceae, Lamiaceae (*Labiatae*), Solanaceae (*Solanum, Lycoperisicon,* etc.), Scrophulariaceae, Bignoniaceae, Pedaliaceae, Orobanchaceae, Gesneriaceae, Lentibulariaceae, Acanthaceae, Myoporaceae, Phrymaceae, Plantaginaceae, Rubiaceae, Caprifoliaceae, Adoxaceae, Valerianaceae, Dipsacaceae, Cucurbitaceae, Campanulaceae, and Asteraceae (*Compositae*).

Examples of monocotyledons include Lemnaceae such as *Spirodela* (*S. polyrhiza*), and *Lemna* (*L. paucicostata*, and *L. trisulcata*), Orchidaceae such as *Cattleya, Cymbidium, Dendrobium, Phalaenopsis, Vanda, Paphiopedilum,* and *Oncidium,* Typhaceae, Sparganiaceae, Potamogetonaceae, Najadaceae, Scheuchzeriaceae, Alismataceae, Hydrocharitaceae, Triuridaceae, Poaceae (*Gramineae*) (*Oryza, Hordeum, Triticum, Secale, Zea,* etc.), Cyperaceae, Arecaceae (*Palmae*), Araceae, Eriocaulaceae, Commelinaceae, Pontederiaceae, Juncaceae, Stemonaceae, Liliaceae (*Asparagus,* etc.), Amaryllidaceae, Dioscoreaceae, Iridaceae, Musaceae, Zingiberaceae, Cannaceae, and Burmanniaceae.

EXAMPLES

The present invention will next be described in more detail by way of examples, which should not be construed as limiting the technical scope of the invention thereto.

Example 1

Production, isolation/purification, and structural analysis of (9R)-11-{(2'S,8'S,10'S,11'R)-2',8'-dihydroxy-7'-oxo-11'-[(Z)-2-pentenyl]-9'-oxa-4'-azatricyclo[6.3.1.0$^{1.5}$]dodec-5'-en-10'-yl}-9-hydroxy-10-oxoundecanoic acid (hereinafter may be referred to as compound (5))

Figure 1:
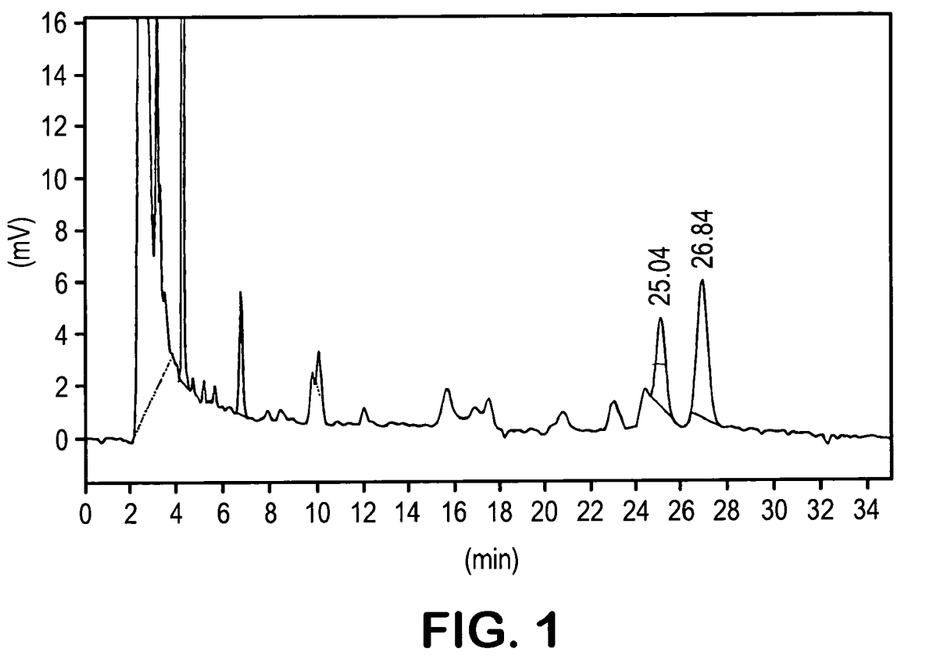
FIG. 1 is a HPLC analysis chart of a reaction product of compound (4) and norepinephrine.

Compound (4) (100 mg) was dissolved in water (500 mL), and (R)-(−)-norepinephrine hydrogentartrate monohydrate (111.3 mg, Wako Pure Chemical Industries, Ltd.) and 1M Tris buffer (pH 8.0, 16.1 mL) were added thereto, followed by incubation at 25° C. for 102 hours. The resultant solution was concentrated under reduced pressure, and the concentrate was subjected to fractionation by means of silica gel column chromatography (Wakogel C-200). By use of a mixture of chloroform, methanol, and water (10:3:1) as an eluting agent, fractionation was further carried out by means of HPLC (column: Capcellpak C-18 UG120, 4.6×250 mm, solvent: 25% acetonitrile+0.1% trifluoroacetic acid, flow rate: 1 mL/min, wavelength: 300 nm). The results of HPLC analysis are shown in FIG. 1. A fraction corresponding to the highest peak (retention time: 26.8 min) was applied to a column having a larger size (Capcellpak C-18 UG120, 10×250 mm) for fractionation. The resultant fraction was freeze-dried, to thereby yield 4.5 mg of compound (5) as yellow crystals.

Figure 2A:
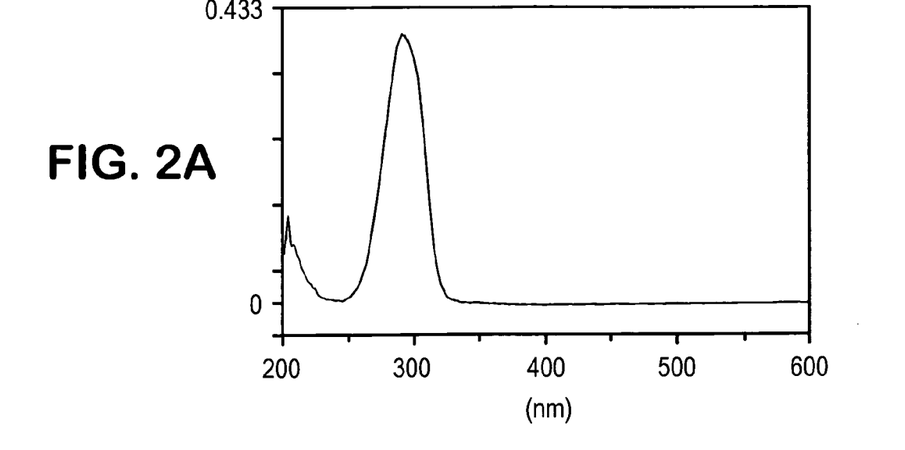
FIGS. 2A, 2B, and 2C show absorption spectra of compounds (5), (4), and norepinephrine, respectively.
Figure 2B:
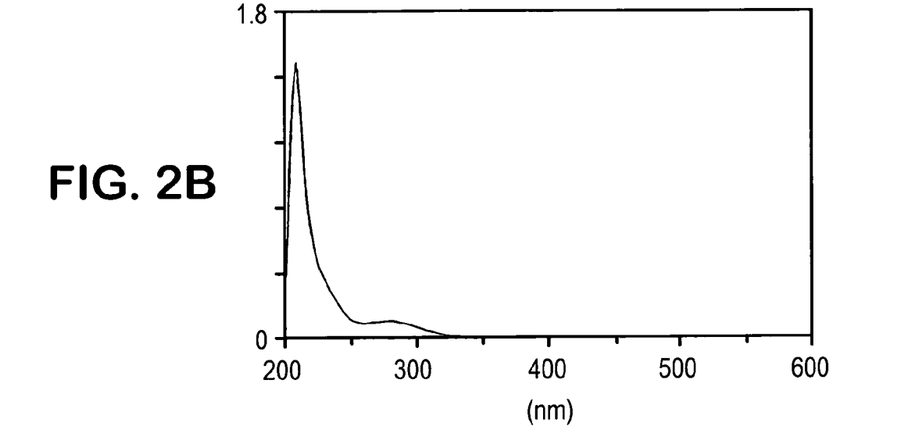
Figure 2C:
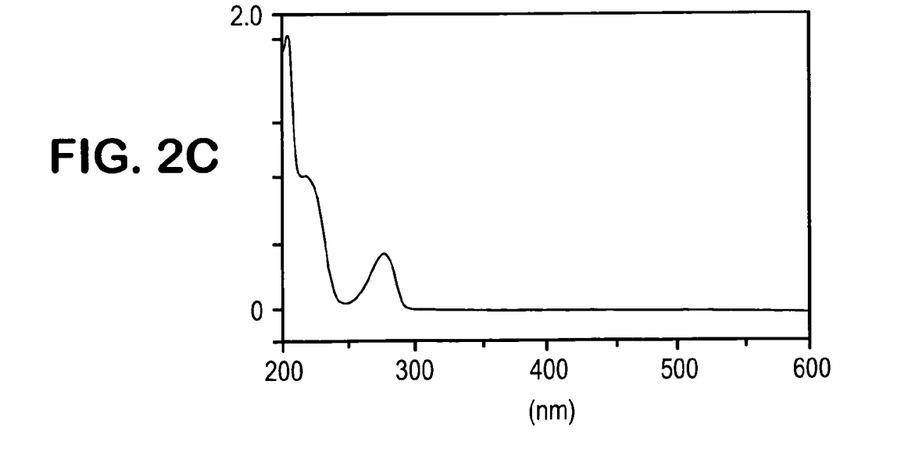

The following instruments were employed for structural analyses of compound (5): A SEPA-300 digital polarimeter (Horiba Ltd.) for measurement of angle of rotation; a UV-2200 spectrophotometer (Shimadzu Corporation) for measurement of absorption spectrum; an FT/IR-5300 (JASCO Corporation) for measurement of IR spectrum; a MAT95Q (Finnigan MAT) for measurement of high-resolution FAB-MS; and an ECP-400 (JEOL) for measurement of $^1$H-NMR and $^{13}$C-NMR. The absorption spectrum measured within the range of 200 nm to 600 nm is shown in FIG. 2 (FIG. 2A, FIG. 2B, and FIG. 2C show absorption spectra of compound (5), compound (4), and norepinephrine, respectively, wherein the X axes represent wavelength (nm), and the Y axes represent absorbance values).

Angle of rotation: $[\alpha]_D^{25}$ +40.5° (c=0.2, MeOH) High-resolution FAB-MS: 494.27789 (M+H)$^{+UV\lambda max(MeOH)}$:292 nm($\epsilon$=12000),205 nm($\epsilon$=3500) IR(KBr, cm$^{-1}$):3400, 1695, 1685, 1630 $^1$H-NMR(400 MHz, CD$_3$OD):$\delta$1.03(3H,t,J=7.3, 5"-H$_3$), 1.11-1.32(8H,4,5,6,7-H$_2$), 1.22(1H,m,3-H), 1.59 (1H,t,J=12,0,3-H), 1.44(1H,m,11'-H), 1.48, 1.66(both 1H,m, 8-H$_2$), 2.00, 2.10(both 1H,J=12.0,12'-H$_2$), 2.11, 2.65(both 1H,m,1"-H$_2$), 2.17(2H,m,J=7.3,4"-H$_2$), 2.26(2H,t-like,J=7, 3,2-H$_2$), 2.56(1H,dd,J=7.8,17,0,11-H), 2.86(1H,dd,J=5.0, 17,0,11-H), 3.43(1H,d,J=13.0,3'-H), 3.85(1H,dd,J=3.4,13.0, 3'-H), 3.98(1H,dd,J=4.0,7,7,9-H), 4.29(1H,d,J=3.4,2'-H), 4.58(1H,m,10'-H), 5.25(1H,m,2"-H), 5.36(1H,m,3"-H), 5.42(1H,s,6'-H). $^{13}$C-NMR(100 MHz,CD$_3$OD):15.0(C-5"), 22.7(C-4"), 25.7(C-1"), 26.3, 26.4(C-3,4), 31.0, 31.0, 31.0 (C-5,6,7), 33.6(C-12'), 34.9(C-8), 35.7(C-2), 41.5(C-11'), 42.9(C-11), 56.1(C-3'), 59.5(C-1'), 72.6(C-10'), 74.2(C-2'), 79.0(C-9), 95.0(C-6'), 95.8(C-8'), 131.0(C-2"), 134.2(C-3"), 177.3(C-5'), 178.5(C-1), 189.0(C-7'), 213.1(C-10).

Assignments of proton and carbon signals were determined through measurement of two-dimensional NMR spectra, such as DIFCOSY, HMQC, and HOHAHA spectra. Comparison of the thus-obtained data with data of compound (4) (described in Japanese Patent Application Laid-Open (kokai) No. 11-29410 and Yokoyama et al., Plant Cell Physiol., 41, 110-113, 2000) reveals that a signal corresponding to cis-olefin at the 12-position of compound (4) had disappeared, suggesting addition of some compound to compound (5) at the 12-position.

When compound (5) was acetylated by use of acetic anhydride/pyridine, a tetraacetate derivative of compound (5) was obtained, proving that compound (5) has four active protons. By comparison of $^1$H-NMR data of the tetraacetate derivative with those of compound (5), signals corresponding to protons at the 9-, 2'-, and 3'-position of compound (5) were found to have shifted to a lower magnetic field side, whereas the proton signal at the 10'-position was not found to have shifted. Therefore, compound (5) is considered to have an ether-linkage at the 10'-position. In addition, these results and detailed analyses of HMBC spectra indicate that compound (5) has a tricyclic structure. Moreover, when NOESY and GOESY spectra of compound (5) were measured, NOEs were found to be observed, for example, between the 11'-position proton and the 2'-, 3'-, and 10'-position protons; between the 10'-position proton and the 6'-position proton; and between the 12'-position axial proton and the 1"-position proton. As a result, 3-dimensional configuration of the cyclic moiety of compound (5) is clearly recognized.

In order to determine the absolute configuration of the 9-position of compound (5), first, absolute configuration of the 9-position of compound (4) which had been obtained through enzyme synthesis was analyzed. Methyl ester reductant of compound (4) was reacted with (R)-(+)- or (S)-(−)-2-methoxy-2-trifluoromethylphenylacetic acid (MTPA) in the presence of 1-ethyl-3-(3-dimethylaminopropyl)carbodiimide hydrochloride and 4-dimethylaminopyridine, whereby respective (R)- or (S)-MTPA ester was obtained. The MTPA esters were applied to the modified Mosher method (Ohtani et al., J. Am. Chem. Soc., 113, 4092-4096, 1991). The results indicate that compound (4) obtained through enzyme synthesis is a mixture of 70% (9R)- and 30% (9S)-optical isomers.

Each of (9R)- and (9S)-optical isomers of compound (4) which had been fractionated by use of a chiral column was reacted with norepinephrine. As a result, only (9R)-configuration of compound (4) was found to yield compound (5).

From the above-described data, the structure of compound (5) is determined as follows.

Example 2

Measurement of Flower Bud Formation Promoting Activity of Compounds (4) and (5) in Morning Glory (*Pharbitis nil*)

Seeds (9 g) of morning glory (variety name: Murasaki) were treated with concentrated sulfuric acid for 20 minutes, and then left to stand overnight under running water. Subsequently, the treated seeds were placed on wet sea sand for 24 hours, hilum side up, to thereby form roots. The seeds having roots were planted in sea sand to a depth of 1.5 cm to 2.0 cm, followed by culturing under continuous light (for approximately 5 days).

The whole plants of the morning glory which had put forth leaves through the culture were transferred to a culture solution [$KNO_3$ (250 mg), $NH_4NO_3$ (250 mg), $KH_2PO_4$ (250 mg), $MgSO_4 \cdot 7H_2O$ (250 mg), $MnSO_4 \cdot 4H_2O$ (1 mg), Fe-citrate n-hydrate (6 mg), $H_3BO_3$ (2 mg), $CuSO_4 \cdot 5H_2O$ (0.1 mg), $ZnSO_4 \cdot 7H_2O$ (0.2 mg), $Na_2MoO_4 \cdot 2H_2O$ (0.2 mg), $Ca(H_2PO_4)_2 \cdot 2H_2O$ (250 mg)/distilled water (1,000 mL)].

Compound (4) or compound (5) was sprayed onto the cotyledons of the above morning glory plants at a spray volume of 2 mL per eight plants. The morning glory plants were subjected to treatment in the dark (14 hours), then raised under the application of continuous light at 26° C. for 14 days. On day 14, the number of flower buds of the morning glory plants was counted.

Figure 3:
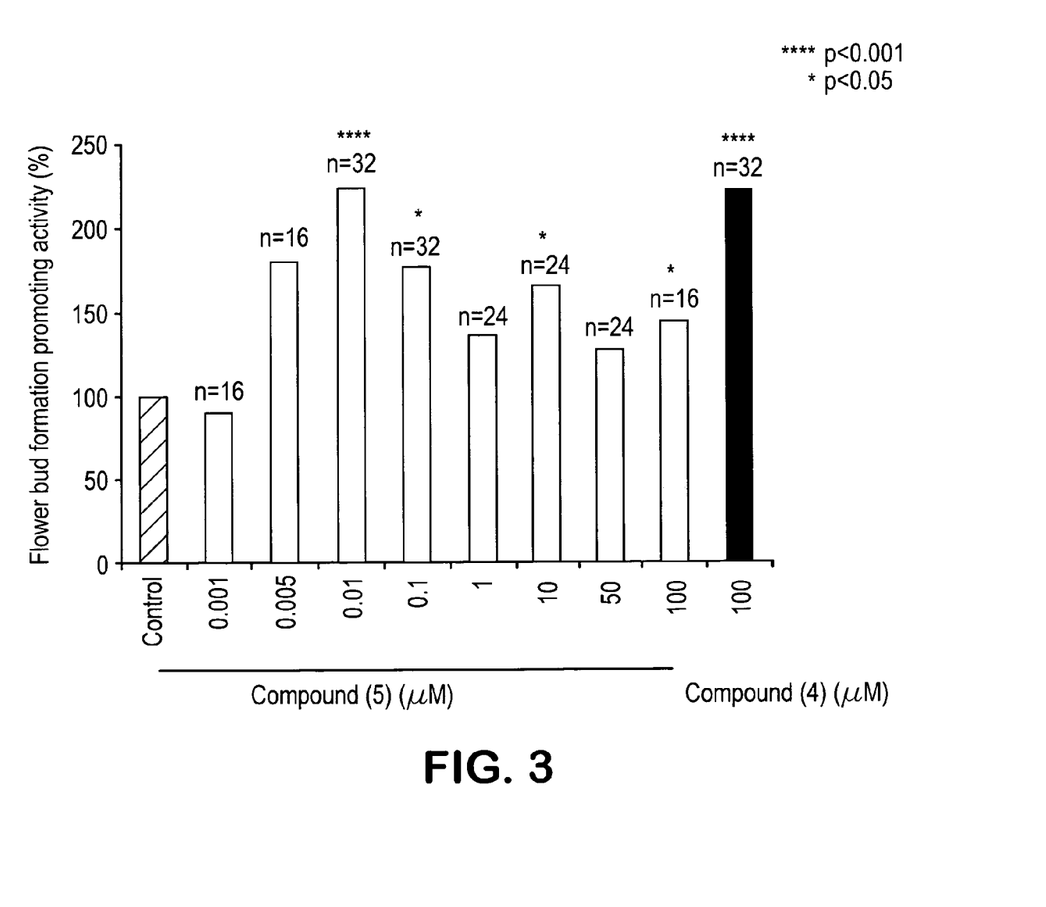
FIG. 3 shows flower bud formation promoting activity of compounds (4) and (5) on morning glory (*Pharbitis nil*)

The results are shown in FIG. 3. As a control, distilled water was sprayed onto a group of plants. Compound (4) was sprayed at a concentration of 100 μM, whereas compound (5) was sprayed at concentrations of 0.001 μM to 100 μM.

Compound (5), having a significantly low concentration as compared with compound (4), exhibited flower bud formation promoting activity, and 0.0 μM compound (5) exhibited the same level of the activity as 100 μM compound (4).

Example 3

Measurement of Flower Bud Formation Promoting Activity of Compound (5) in *Lemna paucicostata* (Duckweed)

The flower bud formation promoting effect of compound (5) was measured on the basis of percent flower generation (%, number of thalluses in which flower bud formation is confirmed/number of all thalluses×100) by use of duckweed P151 plants as model plants.

Compound (4) (0.155 mg) was dissolved in water (0.15 mL), and 10 mM (R)-(−)-norepinephrine hydrogentartrate monohydrate solution (50 μL) and 0.5M Tris buffer (pH 8.0, 25 μL) were added thereto, followed by incubation at 25° C. for 6 hours.

Subsequently, a predetermined volume or amount of the incubated solution or compound (5) prepared in the above Example 1 was added to assay medium (10 mL, no sucrose-containing 1/10 E medium+1 μM benzyladenine) in a flask.

Figure 4:
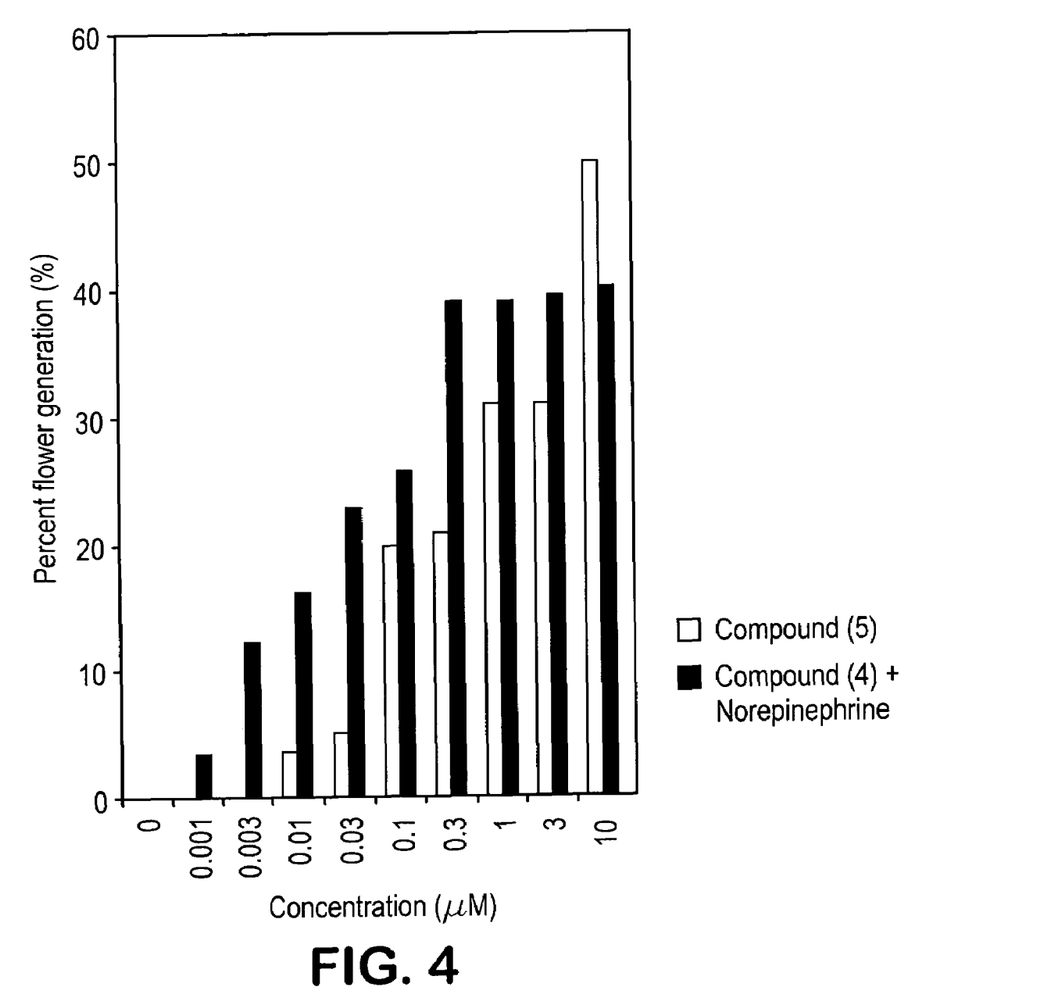
FIG. 4 shows flower bud formation promoting activity of a reaction mixture of compound (4) and norepinephrine, and compound (5) on *Lemna paucicostata* (duckweed)

Onto each of the above assay media, a colony of the P151 plants was planted, followed by incubation at 24-25° C. for 7 days with continuous irradiation by use of a daylight-type fluorescent lamp (Hitachi FL20 SSD, approximately 5 W/m$^2$), to thereby determine the percent flower generation (FIG. 4).

Compound (5) was found to have flower bud formation promoting activity, although the level of the activity of compound (5) was slightly lower than that of a reaction mixture of compound (4) and norepinephrine. This is the first time that a single substance has been found to induce formation of flower bud in duckweed.

Example 4

Measurement of Flower Bud Formation Promoting Activity of Reaction Mixture of Compound (4) and Norepinephrine or Analogues Thereof in *Lemna paucicostata*

The flower bud formation promoting effect of a reaction mixture of compound (4) and norepinephrine (L-norepinephrine) or analogues thereof was measured on the basis of percent flower generation (%, number of thalluses in which flower bud formation is confirmed/number of all thalluses× 100) by use of duckweed P151 plants as model plants.

The employed analogues of norepinephrine are L-epinephrine, dopamine, DL-normetanephrine, 3-O-methyldopamine, 4-O-methyldopamine, homovanillic acid, and vanilloylmandelic acid.

Compound (4) (0.155 mg) was dissolved in water (0.092 mL), and 10 mM (R)-(−)-norepinephrine hydrogentartrate monohydrate solution (50 μL) or a solution (50 μL) containing each of the analogues and 0.5M Tris buffer (pH 8.0, 25 μL) were added thereto, followed by incubation at 25° C. for 24 hours.

Subsequently, the above-incubated solution (10 μL) or a 10-fold diluted solution thereof (10 μL) was added to assay medium (10 mL, no sucrose-containing 1/10 E medium+1 μM benzyladenine) in a flask.

Figure 5:
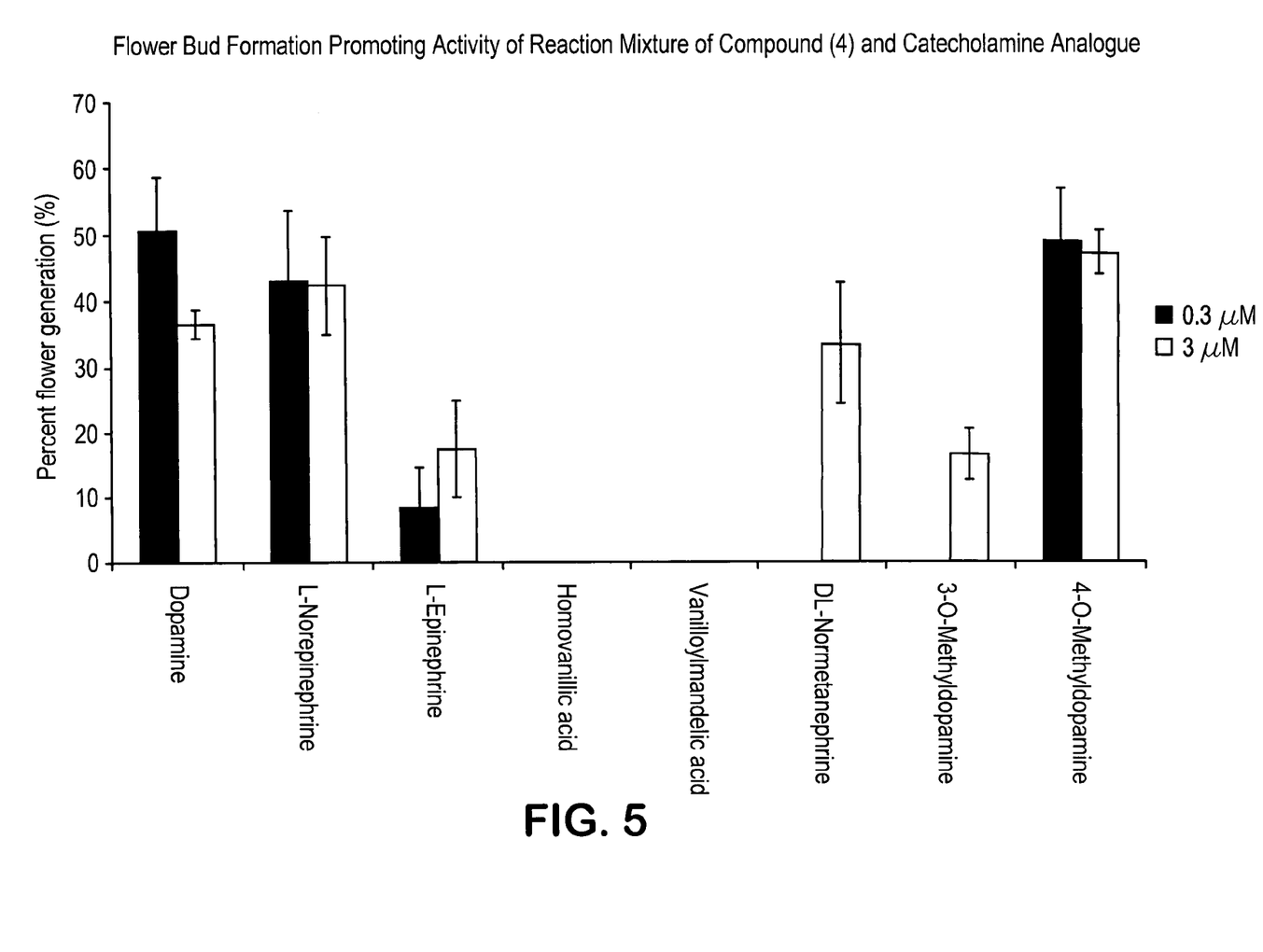
FIG. 5 shows flower bud formation promoting activity of a reaction mixture of compound (4) and norepinephrine or an analogue of norepinephrine.

Onto each of the above assay media, a colony of the P151 plants was planted, followed by incubation at 24-25° C. for 7 days with continuous irradiation by use of a daylight-type fluorescent lamp (Hitachi FL20 SSD, approximately 10 W/m$^2$), to thereby determine the percent flower generation (FIG. 5).

In addition to a reaction mixture of compound (4) and norepinephrine, a reaction mixture of compound (4) and dopamine or 4-O-methyldopamine was found to exhibit high flower bud formation promoting activity. Moreover, a reaction mixture of compound (4) and L-epinephrine, DL-normetanephrine, or 3-O-methyldopamine was found to exhibit a certain level of flower bud formation promoting activity. In contrast, a reaction mixture of compound (4) and homovanillic acid or vanilloylmandelic acid was found to exhibit no appreciable flower bud formation promoting activity.

Example 5

Synthesis of N-[9-hydroxy-10-oxo-12(Z),15(Z)-octadecadienoyl]-L-isoleucine (hereinafter may be referred to as ketol fatty acid derivative (9) of the invention)

9-Hydroxy-10-oxo-12(Z),15(Z)-octadecadienoic acid (compound (4), produced through the "enzyme method" described in paragraph Nos. 0046 to 0065 of Japanese Patent Application Laid-Open (kokai) No. 11-29410, 14.7 mg, 0.0474 mmol) was dissolved in a mixture (5 mL) of DMF and $H_2O$ (9:1). WSC (8.17 mg, 0.9 eq.), HOBt (6.52 mg, 0.9 eq.), and N-methylmorpholine (52.1 µL, 10 eq.) were added thereto, followed by stirring at room temperature for 20 minutes. L-isoleucine lithium salt (13.0 mg, 2 eq.) was added to the stirred solution, followed by a further stirring at room temperature for 2 hours. The resultant solution was subjected to isolation and purification by means of HPLC (Capcellpak C18 UG 120 A, 5 µm, 10 mm×250 mm: solvent [a mixture of $CH_3CN$ (containing 0.085% TFA) and $H_2O$ (containing 0.1% TFA) (1:1)]), to thereby yield 3.0 mg of ketol fatty acid derivative (9) of the invention.

The structure of the ketol fatty acid derivative (9) of the invention was analyzed by use of $^1H$- and $^{13}C$-NMR.

$^1H$-NMR(400 MHz,$CDCl_3$)□0.92(3H,t,J=7.3,5'-$H_3$), 0.96(3H,t,J=7,3,18-$H_3$), 0.98(3H,d,J=7.3,6'-$H_3$), 1.18,1.54 (2H,both m,4H'-$H_2$), 1.20-1.50(all 8H,m,4,5,6,7-$H_2$), 1.52, 1.93(2H, both m,8-$H_2$), 1.60(2H,m,3-$H_2$), 1.83(1H,m,3'-H), 2.08(2H,m,17-$H_2$), 2.23(2H,t-like,J=7,3,2-$H_2$), 2.78(2H,t-like,J=7,0,14-$H_2$), 3.28(2H,t-like,J=6,8,11-$H_2$), 4.23(1H,m, 2'-H), 4.55(1H,m,9-H), 5.29(1H,m,15-H), 5.44(1H,m,16-H), 5.56(1H,m,13-H), 5.61(1H,m,12-H) $^{13}C$-NMR□100 MHz,$CD_3OD$□□12.4(C-5'), 15.4(C-18), 17.0(C-6'), 22.3 (C-17), 26.8, 27.1(C-3,4), 27.5,27,8(C-4',14), 31.0,31.1,31.2 (C-5,6,7), 34.5(C-8), 35.8(C-2), 37.6(C-3'), 39.2(C-11), 77.6 (C-2'), 78.6(C-9), 123.0(C-12), 127.7(C-15), 129.2(C-13), 134.6(C-16), 174.0(C-1'), 176.6(C-1), 203.9(C-10)

and then left to stand overnight under running water. Subsequently, the treated seeds were placed on wet sea sand for 24 hours, hilum side up, to thereby form roots. The seeds having roots were planted in sea sand to a depth of 1.5 cm to 2.0 cm, followed by culturing under continuous light (for approximately 5 days).

The whole plants of the morning glory which had put forth leaves through the culture were transferred to a culture solution [$KNO_3$ (250 mg), $NH_4NO_3$ (250 mg), $KH_2PO_4$ (250 mg), $MgSO_4.7H_2O$ (250 mg), $MnSO_4.4H_2O$ (1 mg), Fe-citrate n-hydrate (6 mg), $H_3BO_3$ (2 mg), $CuSO_4.5H_2O$ (0.1 mg), $ZnSO_4.7H_2O$ (0.2 mg), $Na_2MoO_4.2H_2O$ (0.2 mg), $Ca(H_2PO_4)_2.2H_2O$ (250 mg)/distilled water (1,000 mL)].

While ketol fatty acid derivative (9) of the invention, which was obtained in the above Example 5, or test compounds such as Compound (4) was directly sprayed onto the cotyledons of the above morning glory plants grown in the culture system, the morning glory plants were subjected to treatment in the dark, then raised under the application of continuous light at 26° C. for 16 days. On day 16, the number of flower buds of the morning glory plants was counted (8 plants/group).

The treatment in the dark was performed overnight (for 14 hours).

Figure 6:
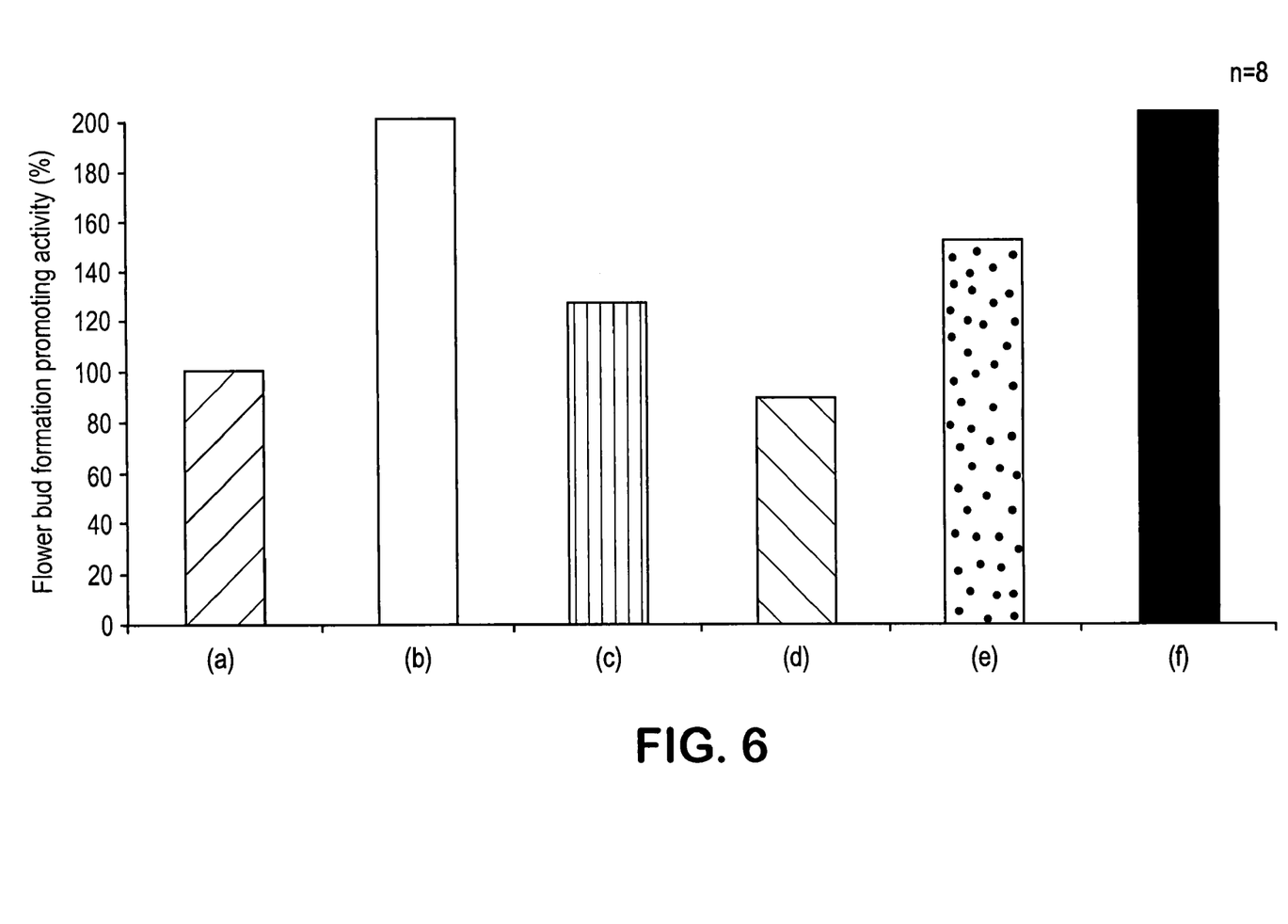
FIG. 6 shows the results of comparison regarding flower bud formation promoting activity, on morning glory, of the ketol fatty acid derivative (9) of the invention and that of compound (4), etc.

In FIG. 6, along the X axis, (a) represents a control (a group of plants sprayed with distilled water), (b) represents a group of plants sprayed with ketol fatty acid derivative (9) (1 µM), (c) represents a group of plants sprayed with compound (4) (1 µM) and L-isoleusine (1 µM), (d) represents a group of plants sprayed with L-isoleusine (1 µM), (e) represents a group of plants sprayed with compound (4) (1 µM), and (f) represents a group of plants sprayed with compound (4) (100 µM). The Y axis represents flower bud formation promoting activity (shown as the percentage of each group to the control group (=100%) in terms of the number of flower buds per plant).

As shown in FIG. 6, ketol fatty acid derivative (9) of the invention exhibits equal or higher flower bud formation promoting effect as compared with compound (4), even when the ketol fatty acid derivative (9) has a lower concentration than compound (4). Since this effect was not observed in group (d) onto which only L-isoleucine was sprayed, the effect is considered to be unique to amide derivatives such as ketol fatty acid derivative (9) of the invention.

Figure 7:
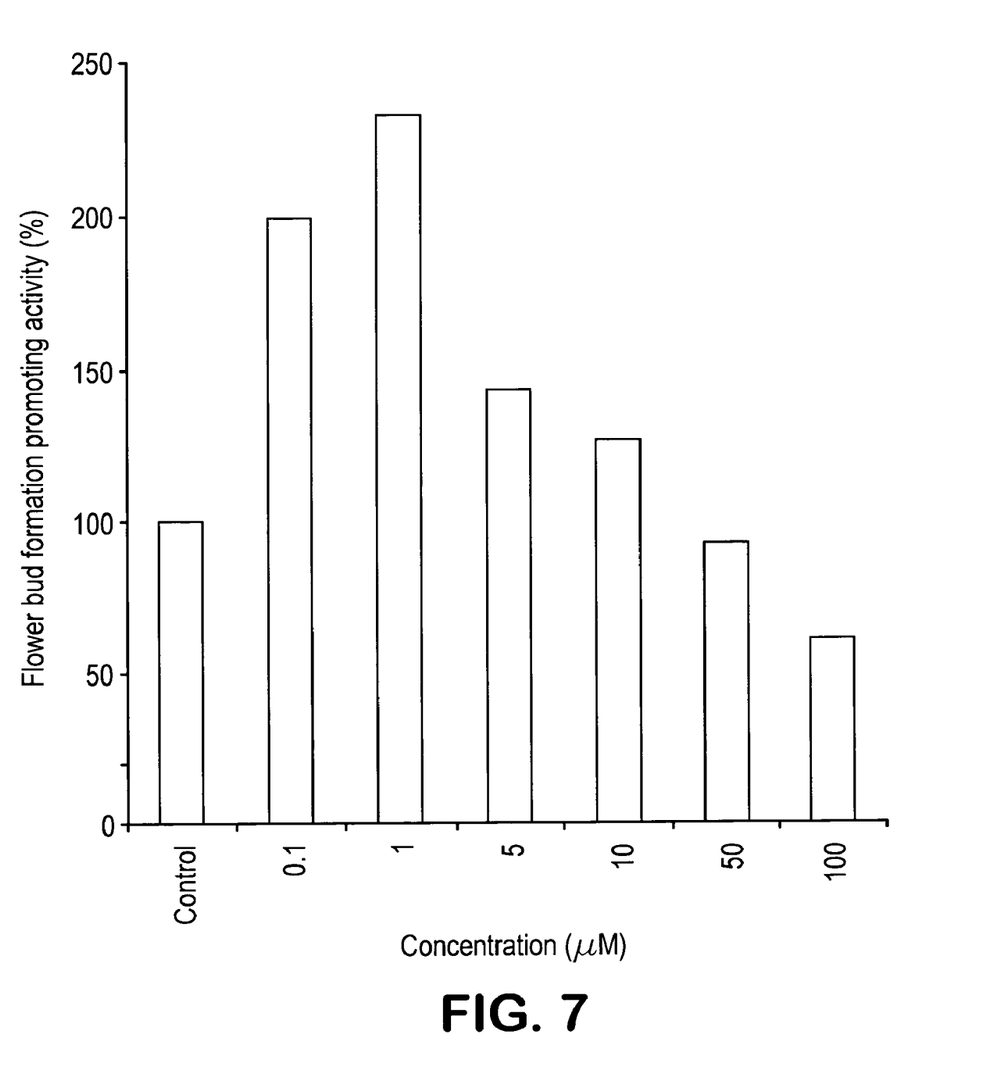
FIG. 7 shows the results of study of flower bud formation promoting activity, on morning glory, of the ketol fatty acid derivative (9) of the invention in relation to the administration concentration of the derivative.

FIG. 7 shows data used to determine the optimum administration concentration of ketol fatty acid derivative (9) of Ketol fatty acid derivative (9)

Example 6

Study of Flower Bud Formation Promoting Activity of Ketol Fatty Acid Derivative II of the Invention in Morning Glory (*Pharbitis nil*)

Seeds (9 g) of morning glory (variety name: Murasaki) were treated with concentrated sulfuric acid for 20 minutes, the invention. The ketol fatty acid derivative (9) was sprayed onto morning glory plants in the same manner as that outlined above, at concentrations of 0 µM (control), 0.1 µM, 1 µM, 5 µM, 10 µM, 50 µM, and 100 µM shown in the abscissa of FIG. 7 (8 to 24 plants were employed for one concentration), whereby the flower bud formation promoting activity (%) was studied.

As is shown in FIG. 7, the optimum administration concentration of ketol fatty acid derivative (9) of the invention was found to be approximately 1 µM.

INDUSTRIAL APPLICABILITY

The present invention provides substances endowed with excellent plant growth regulating effect and processes for preparing the substances. Moreover, the invention provides plant growth regulators containing any of the substances as the active component.

The invention claimed is:

1. An α-ketol unsaturated fatty acid amide derivative represented by the following formula (6):

(6)

wherein $R^7$ represents $C_{1-17}$ alkyl or $C_{2-17}$ unsaturated hydrocarbyl having 1 to 5 double bonds (wherein the number of double bonds does not exceed the total number of carbon-carbon bonds); $R^8$ represents hydrogen or a side chain of α-amino acid; $R^9$ represents α-ketolalkylene; and $R^{10}$ represents a divalent linear hydrocarbyl of the following formula:

wherein L, m, and k are integers, with m being 0 or 1 and L+k being 1 to 15.

2. The α-ketol unsaturated fatty acid amide derivative as recited in claim 1, wherein m is 0 and L+k is 3 to 10 inclusive.

3. The α-ketol unsaturated fatty acid amide derivative as recited in claim 1, wherein L+k is 7.

4. The α-ketol unsaturated fatty acid amide derivative as recited in claim 1, wherein $R^7$ is an alkenyl group represented by the following formula:

wherein $R^{11}$ is $C_{1-7}$ linear alkyl.

5. The α-ketol unsaturated fatty acid amide derivative as recited in claim 4, wherein $R^{11}$ is ethyl.

6. The α-ketol unsaturated fatty acid amide derivative as recited in claim 1, wherein the double bonds are of the cis-form.

7. The α-ketol unsaturated fatty acid amide derivative as recited in claim 1, wherein a carbon atom on the amide bonding side of $R^9$ is bonded to a hydroxyl group.

8. The α-ketol unsaturated fatty acid amide derivative as recited claim 1, wherein $R^8$ is a side chain of an L-form neutral amino acid.

9. The α-ketol unsaturated fatty acid amide derivative as recited in claim 1, which is N-[9-hydroxy-10-oxo-12(Z),15(Z)-octadecadienoyl]-L-isoleucine.

* * * * *